United States Patent [19]

de Ruiter

[11] Plant 4,018

[45] Feb. 22, 1977

[54] ROSE PLANT

[75] Inventor: Gijsbert de Ruiter, Hazerswoude, Netherlands

[73] Assignee: Jackson & Perkins Co., Medford, Oreg.

[21] Appl. No.: 649,505

[22] Filed: Jan. 15, 1976

[51] Int. Cl.[2] ..... A01H 5/00

[52] U.S. Cl. ..... Plt./27

[58] Field of Search ..... Plt./27

*Primary Examiner*—Robert E. Bagwill

*Attorney, Agent, or Firm*—Klarquist, Sparkman, Campbell, Leigh, Hall & Whinston

EXEMPLARY CLAIM

1. A new and distinct cultivar of rose of the floribunda class, substantially as herein shown and described, characterized particularly as to novelty by the unique combination of its uniform shape; upright and heavily branched plant habit; large, leathery, mildew resistant foliage; abundant flowers of Blood Red (W) color.

No Drawings

The present invention relates to a new and distinct cultivar of rose plant of the floribunda class which was originated by crossing the cultivar, Lilli Marlene, U.S. Plant Pat. No. 1,986, with pollen of an unnamed cultivar.

The primary objective of this breeding was to produce a cultivar of the floribunda class having a uniform habit of growth, relatively large, non-fading red blooms, with foliage resistant to various diseases. This objective was fully achieved along with other desirable traits as evidenced by the following unique combination of characteristics which are outstanding in the new cultivar and which distinguish it from its parents as well as from all other cultivars of which I am aware:

1. A vigorous, well branched and upright plant of approximately three feet in height at Irvine, Calif., resembling the cultivar Lilli Marlene but having a more regular growth and better branching.
2. A strong resistance to Rose Powdery Mildew.
3. An abundance and continuity of blooms of a Blood Red (W) color.
4. A more upright habit of growth than the cultivar Europeana, U.S. Plant Pat. No. 2,540, which it resembles.
5. Distinctly different color of the anthers and filaments than in Europeana as detailed below.

Asexual reproduction of this new cultivar by budding as performed at Hazerswoude, Holland, and at Irvine, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed Parent.*—Lilli Marlene, U.S. Plant Pat. No. 1,986.

*Pollen Parent.*—Unnamed seedling of Europeana, U.S. Plant Pat. No. 2,540 by Kimono.

Classification:

*Botanical.*—Rose hybrid.

*Commercial.*—Floribunda.

FLOWER

Observations made from specimens grown at Irvine, Calif., October, 1975.

Blooming Habit: Continuous.

Bud:

*Size.*—Approximately ¾" to 1" when petals start to unfurl.

*Form.*—Pointed ovoid, broad base.

*Color.*—When sepals first divide slightly darker than Cardinal Red (822). When half blown upper side of petals between Cardinal Red (822) and Blood Red (820). Lower side of petals near Cardinal Red (822/3).

*Sepals.*—Color: Outer surface Scheeles Green (860/1) overlaid in part with Garnet Brown (00918/3) with scattered stipitate glands. Inner surface heavy covering of white tomentum over a color similar to outer surface. Three appendaged sepals lightly appendaged. Two unappendaged sepals hairy edged.

*Receptacle.*—Color: Scheeles Green (860/1) overlaid partly with a color lighter than Garnet Brown (00918/3). Shape: apple. Surface: smooth, except having a few glands.

*Peduncle.*—Length: Short. Surface: glandular. Color: light green, bronzy. Strength: stiff, erect.

*Opening.*—Outer petals reflex without quilling, center petals remain curled over flower parts until flower is fully open.

Bloom:

*Size.*—Medium. Average open size 2½".

*Borne.*—In clusters, flat or irregular.

*Stems.*—Medium.

*Form.*—When first open, flat. Permanence, outer petals edges slightly curled.

*Petalage.*—Number of petals under normal conditions 20–25.

*Color.*—Center of flower: Upper side of petals near Blood Red (820). Reverse side of petals near Cardinal Red (822/3). Base of petals small area of white. General tonality from a distance Blood Red (820). Variegations, some darkening of petal edges after several days open.

*Discoloration.*—General tonality at end of first day, little difference from freshly opened. On third day, only slightly darker than Blood Red (820) with some darker edges.

*Fragrance.*—Very slight.

Petals:

*Texture.*—Thick.

*Shape.*—Round.

*Form.*—Tips slightly recurved.

*Arrangement.*—Loosely imbricated. Petaloids in center, few.

*Persistence.*—Drop off cleanly.

*Lastingness.*—On the plant — very long. As cut flower — very long.

Reproductive Parts:

*Anthers.*—Medium, many. Color: near Chinese Yellow (606). Arrangement: regular around styles.

*Filaments.*—Color: near Uranium Green (63/2).

*Pollen.*—Lemon yellow.

*Styles.*—Color: near Uranium Green (63/2).

*Stigmas.*—Yellow.

PLANT

Form: Bush.

Growth: Very vigorous, upright, branching.

Foliage: Number of leaflets on normal mid-stem leaves usually 7.

*Size.*—Large.

*Quantity.*—Abundant.

*Color.*—New foliage: lighter than Spinach Green (0960/3) heavily overlaid with a color lighter than Garnet Brown (00918/3). Old foliage: near Spinach Green (0960/1).

*Shape.*—Oval.

*Texture.*—Leathery.

*Edge.*—Serrated.

*Serration.*—Single, large.

*Petiole.*—(*rachis*).—Color: green with upper edges being near Garnet Brown (00918/3). Underside: prickles.

*Stipules.*—Long and broad, edges having a few stipitate glands.

*Disease Resistance.*—Resistant to mildew under normal growing conditions at Irvine, Calif.

Wood:

*New Wood.*—Color: light green, with brownish overlay. Bark, smooth.

*Old Wood.*—Color: green. Bark, smooth.

Prickles:

*Quantity.*—On main stalks from base, many. On laterals from stalk, many.

*Form.*—Broad base, long, hooked downward.

*Color When Young.*—Brown.

*Position.*—Irregular.

Small Prickles:

*Quantity.*—On main stalks, many. On laterals, many.

*Color.*—Brown.

I claim:

1. A new and distinct cultivar of rose of the floribunda class, substantially as herein shown and described, characterized particularly as to novelty by the unique combination of its uniform shape; upright and heavily branched plant habit; large, leathery, mildew resistant foliage; abundant flowers of Blood Red (W) color.

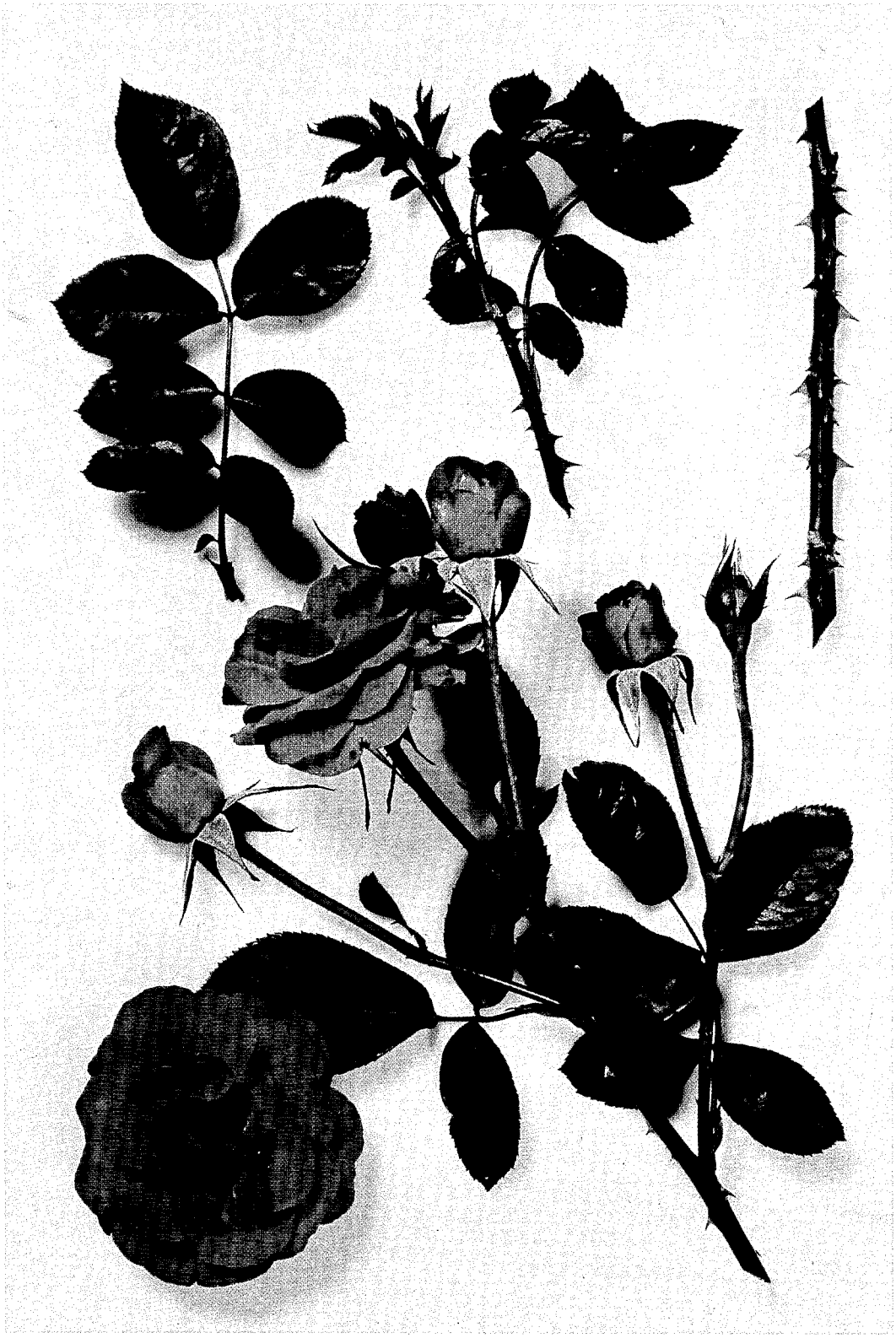

* * * * *